US012521199B2

(12) United States Patent
Zerjav et al.

(10) Patent No.: US 12,521,199 B2
(45) Date of Patent: Jan. 13, 2026

(54) NASAL GUARD FOR USE DURING NASAL SINUS AND SKULL BASE SURGERY

(71) Applicants: The Trustees of Dartmouth College, Hanover, NH (US); Dartmouth-Hitchcock Clinic, Lebanon, NH (US)

(72) Inventors: Dylan C. Zerjav, Hanover, NH (US); Joseph A. Paydarfar, Hanover, NH (US); Yuan Shi, Hanover, NH (US); Ryan J. Halter, Orford, NH (US)

(73) Assignees: The Trustees of Dartmouth College, Hanover, NH (US); Dartmouth-Hitchcock Clinic, Lebanon, NH (US)

( * ) Notice: Subject to any disclaimer, the term of this patent is extended or adjusted under 35 U.S.C. 154(b) by 486 days.

(21) Appl. No.: 17/676,702

(22) Filed: Feb. 21, 2022

(65) Prior Publication Data

US 2022/0280257 A1 Sep. 8, 2022

Related U.S. Application Data

(60) Provisional application No. 63/152,129, filed on Feb. 22, 2021.

(51) Int. Cl.
*A61B 90/00* (2016.01)
*A61B 17/24* (2006.01)

(52) U.S. Cl.
CPC .............. *A61B 90/04* (2016.02); *A61B 17/24* (2013.01); *A61B 2090/0427* (2016.02)

(58) Field of Classification Search
CPC ..... A61B 90/04; A61B 17/24; A61B 17/3423; A61B 2014/246; A61B 2217/005;
(Continued)

(56) References Cited

U.S. PATENT DOCUMENTS 2,831,487 A * 4/1958 Tafilaw ................. A61M 25/02 128/206.28
2,859,748 A * 11/1958 Hudson ................. A61M 16/06 128/206.28

(Continued)

FOREIGN PATENT DOCUMENTS

WO 2021240022 12/2021

OTHER PUBLICATIONS

Gallo, 0., Locatello, L.G., Mazzoni, A et al. The central role of the nasal microenvironment in the transmission, modulation, and clinical progression of SARS CoV2 infection. Mucosa/ Immunol (Nov. 26, 2020) https://doi .org/10.1038/s41385020 003592.

(Continued)

*Primary Examiner* — Adam Baker
(74) *Attorney, Agent, or Firm* — Loginov & Associates, PLLC; William A. Loginov

(57) ABSTRACT

This invention provides a nasal guard, which can be constructed according to various manufacturing techniques (e.g. molding. 3D printing, etc.) for use during nasal sinus and skull base surgery to reduce aerosolized transmission to protect surgical staff, conserve the volatile supply of personal protective equipment (PPE) and reduce the introduction of particles into the operating room. The novel nasal guard, according to embodiments of this invention, can be readily applied to the patient's nose/nasal region during surgery and, while exposing the nostrils for access by surgical procedures, reduces aerosol emission from the nares. This allows for an adequate seal on a variety of face sizes/shapes without impeding access for surgical tools and/or does not otherwise interfere with surgical approach. The nasal guard herein is also compatible with standard suction equipment. The nasal guard is easy-to-use and
(Continued)

ergonomic, and can be (is) constructed from biocompatible materials.

20 Claims, 7 Drawing Sheets

(58) Field of Classification Search
CPC ............ A61B 17/3494; A61B 17/3496; A61B 2017/00336; A61B 2017/246; A61B 2562/18; A61B 23/06; A61B 5/682; A61F 5/56; A61F 5/08; A61M 15/085; A61M 16/0497; A61M 16/06–0694; A61M 2025/0226; A61M 25/02; A61M 25/028; A61M 16/0666; A61M 16/0683; A61M 16/0672; A61M 16/0677; A61M 16/127; A61M 16/0461; A61M 1/71; A61M 1/77; A61M 1/84; A61M 27/00; A61M 2210/0618; A61M 39/02; A61M 2039/0279; A61M 2039/0282; A61M 2039/0288; A41D 13/11–1192
USPC .......................................................... 128/846
See application file for complete search history.

(56) References Cited

U.S. PATENT DOCUMENTS 3,814,103 A * 6/1974 Fettel ................ A61M 16/0666 128/207.18
5,752,511 A * 5/1998 Simmons .......... A61M 16/0497 128/207.18
6,561,190 B1 * 5/2003 Kwok .................... A62B 18/02 128/205.24
8,381,732 B2 2/2013 Daly
8,874,251 B2 * 10/2014 Thornton ................ G06F 30/00 700/118
11,583,654 B1 * 2/2023 Golub ............... A61M 16/0816
2006/0081248 A1 * 4/2006 McDonald ............ A61M 16/06 128/205.25
2013/0096382 A1 4/2013 Alexander
2015/0164552 A1 * 6/2015 Chen ...................... A61B 90/00 600/204
2016/0345863 A1 * 12/2016 Johnson ............ A61M 16/0666
2017/0007795 A1 * 1/2017 Pedro ...................... A61B 5/082
2017/0189635 A1 * 7/2017 Beard ............... A61M 16/0051
2019/0038863 A1 2/2019 Chang
2021/0330922 A1 * 10/2021 Boston .............. A61M 16/0683

OTHER PUBLICATIONS

Workman, AD, Welling, DB, Carter, BS, et al. Endonasal instrumentation and aerosolization risk in the era of COVID19: simulation, literature review, and proposed mitigation strategies, International Forum of Allergy & Rhinology, vol. 10, No. 7 (Jul. 2020); 10: 798 805 https://onlinelibrary.wiley.com/doi/10.1002/alr.22577.
Zou, L. et al. SARSCoV2 viral load in upper respiratory specimens of infected patients. N. Engl. J. Med (Mar. 19, 2020) https://doi.org/10.1056/NEJMc2001737.
Viera-Artiles et al. A novel aerosolisation mitigation delice for endoscopic sinus and skull base surgery in the COVID-I9 era. European Archives of Oto-Rhino-Laryngology. vol. 278. No. 6. Nov. 16, 2020 (Nov. 16, 2020).

* cited by examiner

NASAL GUARD FOR USE DURING NASAL SINUS AND SKULL BASE SURGERY

RELATED APPLICATIONS

This application claims the benefit of U.S. Provisional Application Ser. No. 63/152,129, entitled NASAL GUARD FOR USE DURING NASAL SINUS AND SKULL BASE SURGERY, filed Feb. 22, 2021, the teachings of which are expressly incorporated herein by reference.

FIELD OF THE INVENTION

This invention relates to surgical instruments, and more particularly to surgical instruments used to guard against contamination and release of airborne pathogens.

BACKGROUND OF THE INVENTION

SARS-CoV-2 virus—the causative agent of COVID-19—spreads via respiratory droplets. See Zou, L. et al. SARS-CoV-2 viral load in upper respiratory specimens of infected patients. N. Engl. J. Medhttps://doi.org/10.1056/NEJMc2001737 (2020). Notably, nasal mucosa has been found to contain the highest viral load of upper respiratory tissues, and hence is a significant repository for the virus and significantly facilitates its spread. See Gallo, O., Locatello, L. G., Mazzoni, A. et al. The central role of the nasal microenvironment in the transmission, modulation, and clinical progression of SARS-CoV-2 infection. Mucosa/Immunol (2020). https://doi.org/10.1038/s41385-020-00359-2. Additionally, it has been determined that detectable viral loads exist in the nose in both symptomatic and asymptomatic people up to 21 days. Hence Due to the surgical site and aerosolization of particles during surgical drilling, nasal sinus and skull base surgery are considered particularly high-risk procedures in terms of transmission. See Workman, A. D., Welling, D. B., Carter, B. S., et al. Endonasal instrumentation and aerosolization risk in the era of COVID-19: simulation, literature review, and proposed mitigation strategies. Int Forum Allergy Rhino/. 2020; 10: 798-805.

Thus, it is desirable to provide a device, and associated method for use, that assists in reducing the change of exposure during such surgical procedures.

SUMMARY OF THE INVENTION

This invention overcomes disadvantages of the prior art by providing a nasal guard, which can be constructed according to various manufacturing techniques (e.g. molding. 3D printing, etc.) for use during nasal sinus and skull base surgery to reduce aerosolized transmission to protect surgical staff, conserve the volatile supply of personal protective equipment (PPE) and reduce the introduction of particles into the operating room. The novel nasal guard, according to embodiments of this invention, can be readily applied to the patient's nose/nasal region during surgery and, while exposing the nostrils for access by surgical instruments serves to significantly reduce aerosol emission from the nares. Hence, the novel design allows for an adequate seal on a variety of face sizes and shapes without impeding access for surgical tools and/or does not otherwise interfere with surgical approach. The nasal guard herein is also compatible with standard suction equipment. More generally, the nasal guard is easy-to-use and ergonomic, and can be (is) constructed from biocompatible materials.

In an illustrative embodiment, a nasal guard for placement on a patient's face during surgical procedures is provided. A rigid or semi-rigid top section is provided with openings/channels for access to the nostrils by surgical instruments. A vacuum port is also provided in communication with the channels. A soft pliable seal base is located between the rigid or semi-rigid section and the patient's face. Illustratively, a frustoconical guiding shroud extends outwardly from each of the channels, respectively. The top section can be constructed from a polymer material. And/or the base can be constructed from a silicone-based compound. Additionally, the base can define a contoured edge constructed and arranged to sealingly conform to the patient's face around a nose thereof. Surgical instruments for use with the nasal guard can include, but are not limited to, nasal endoscopes. The top section can further define a cavity that allows communication by vacuum flow between the channels and the vacuum port. The vacuum port can be located on a top of the top section adjacent to a side thereof opposite the channels and the vacuum port is constructed and arranged for removable attachment of a vacuum line.

In an illustrative embodiment, a method for reducing particulate discharge from a patient during nasal procedures is provide. The method includes the step of engaging a nose region of the patient with a nasal guard having a rigid or semi-rigid top section and a resilient base section that forms a seal around the base of the nose. A vacuum is applied through a port located on the top section, and a nostril of the nose is engaged by an elongated instrument through an opening in the top section that confronts the nostril. The instrument can comprise a nasal endoscope. Additionally, as described above, the top section can be constructed from a polymer material, and/or the base can be constructed from a silicone-based compound. The nasal guard can be provided to practitioners in a plurality of sizes adapted to fit a given patient's face, such that the practitioner can, more particularly, select from a plurality of sizes of base to achieve a conforming fit to the nose region.

BRIEF DESCRIPTION OF THE DRAWINGS

The invention description below refers to the accompanying drawings, of which.

DETAILED DESCRIPTION

Figure 1:
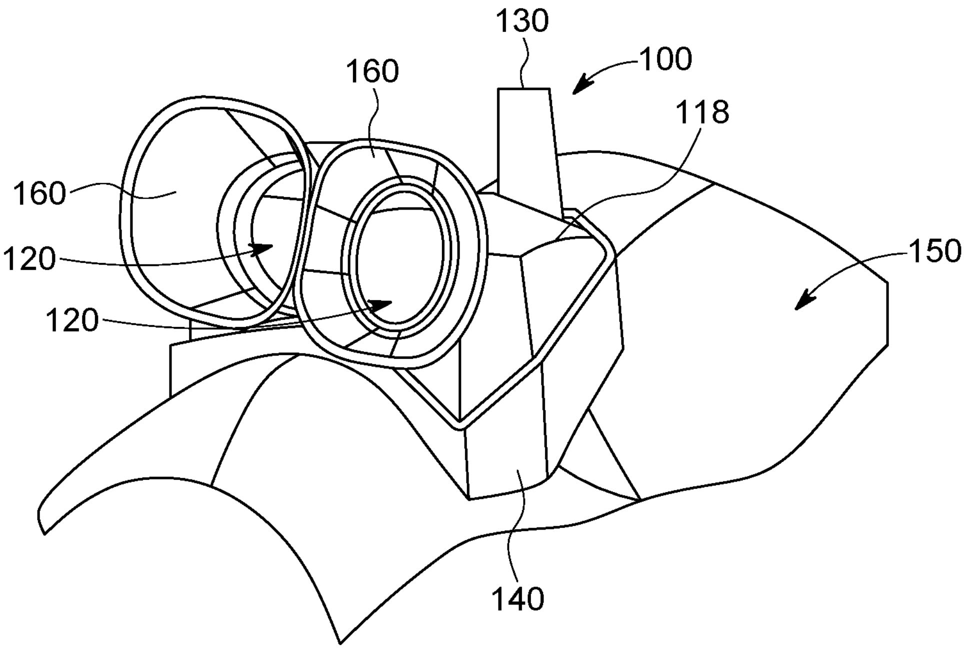
FIG. 1 is a perspective view of a nasal guard mounted on a patient's face, shown in fragmentary view around the nasal region, according to an illustrative embodiment, showing a rigid or semi-rigid top portion and a pliable/resilient (e.g. silicone) bottom gasket portion that engages the patient's face to form a seal therewith.

FIG. 1 shows a nasal guard 100 having the rigid (or semi-rigid) top half 110 which contains an opening 120 at each nostril for surgical access and an embedded vacuum tube 130 adjacent a far end of the top half 110, opposite the openings 120. The top half defines, generally an inlet at each forward opening and an outlet at a standard vacuum adapter. The bottom half 140 of the nasal guard 100 is a (e.g.) silicone gasket to create a seal along the patient's face 150. Note that a vacuum port 130 extends upwardly from the rear top of the rigid top half 110 for connection of a conventional vacuum line (e.g. a flexible silicone tubing) normally found in a surgical setting. By way on non-limiting example, each of the openings 120 includes a unitarily molded or integrally applied, flared shroud 160, that assists in preventing drippage, and guides instruments into the respective opening 120. The size and shape of each shroud 160 is highly variable. In an exemplary embodiment, each shroud 160 defines a frustoconical shape that flares outwardly away from the guard top half 110.

Figure 2:
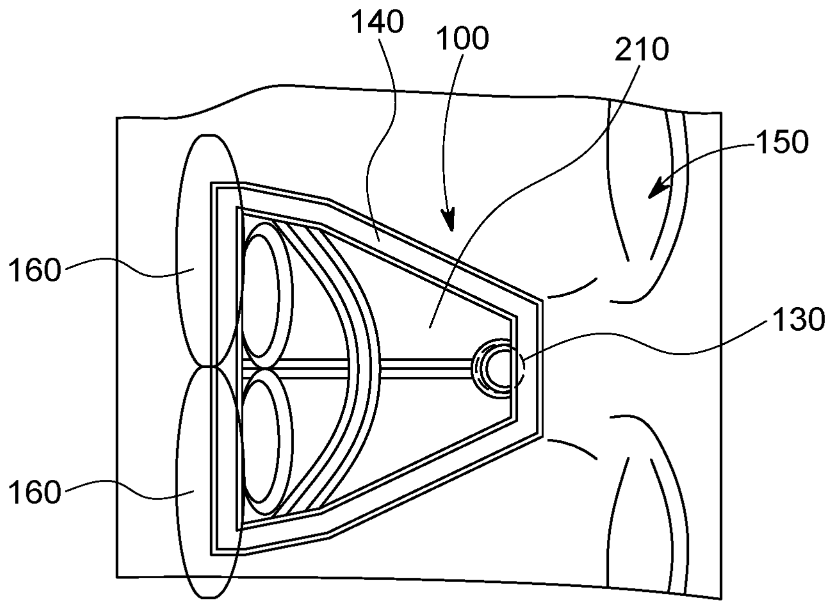
FIG. 2 is a cutaway top view of the nasal guard of FIG. 1 showing an internal vacuum channel within the rigid/semi-rigid portion.

FIG. 2 shows a top view of the nasal guard 100 of FIG. 1 with the outer housing 110 cut away showing the internal vacuum channel/cavity 210 that is in communication with the vacuum port 130 (shown in phantom), and allows for the evacuation of material from/via the interior channel/cavity 210 of the guard.

Figure 3:
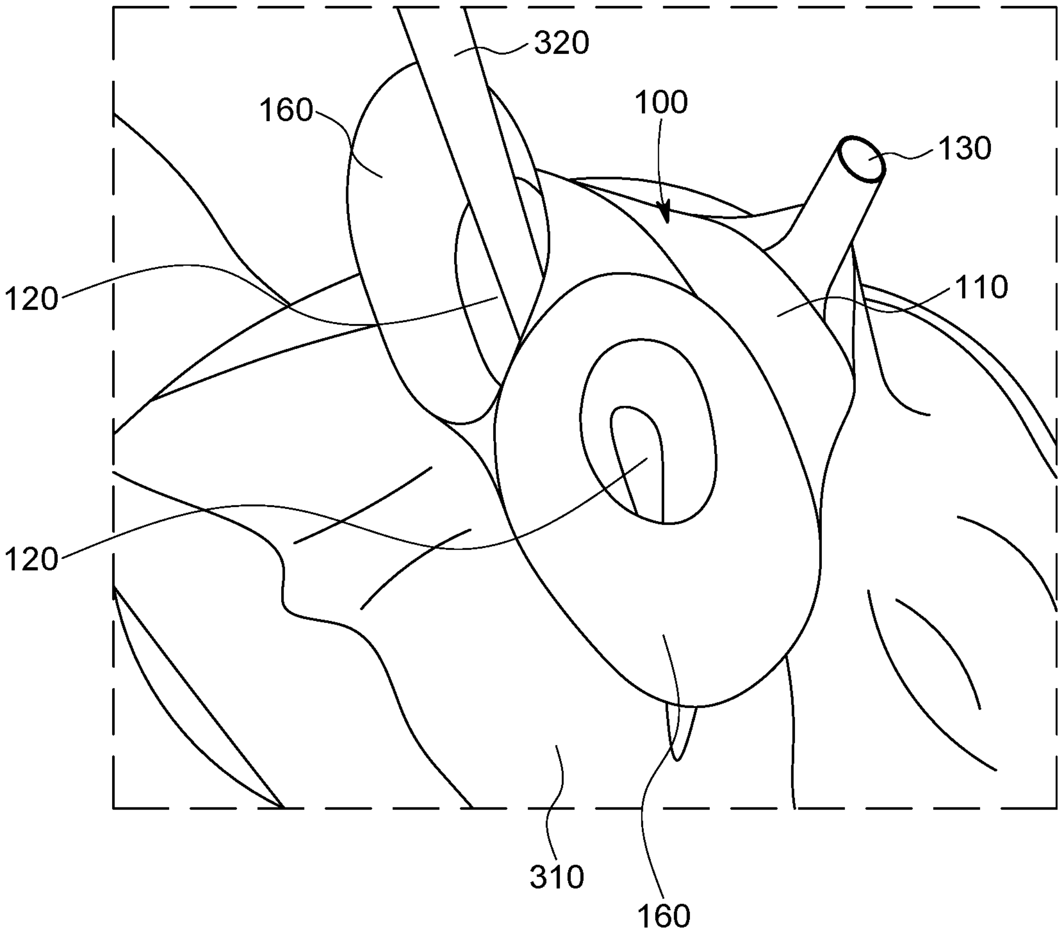
FIG. 3 is an image of the nasal guard of FIG. 1 mounted with respect to an exemplary patient's nasal region.

FIG. 3, shows an image of the nasal guard of FIG. 1 mounted on an exemplary patient's face 310, and engaging the nasal region/nose in a sealing manner. By way of non-limiting example, the nasal guard 100 is shown supporting and guiding a nasal endoscope 320 through respective openings 120 in place in a manner that reduces the potential for contamination while allowing for effective surgical access. Note that the openings 120 confront the nostril regions include the above-described unitary, frustoconical shrouds 160, respectively, to assist in insertion of instruments. The pathways into the nostrils are each in communication with the vacuum flow via the inlet 130.

The nasal guard can be constructed using a variety of techniques, with either one or more standard sizes (via molding, etc.) or a custom sizing achieved, for example, by using 3D printing techniques with shape/sizing inputs derived from the contours of the patient's face.

Figure 4:
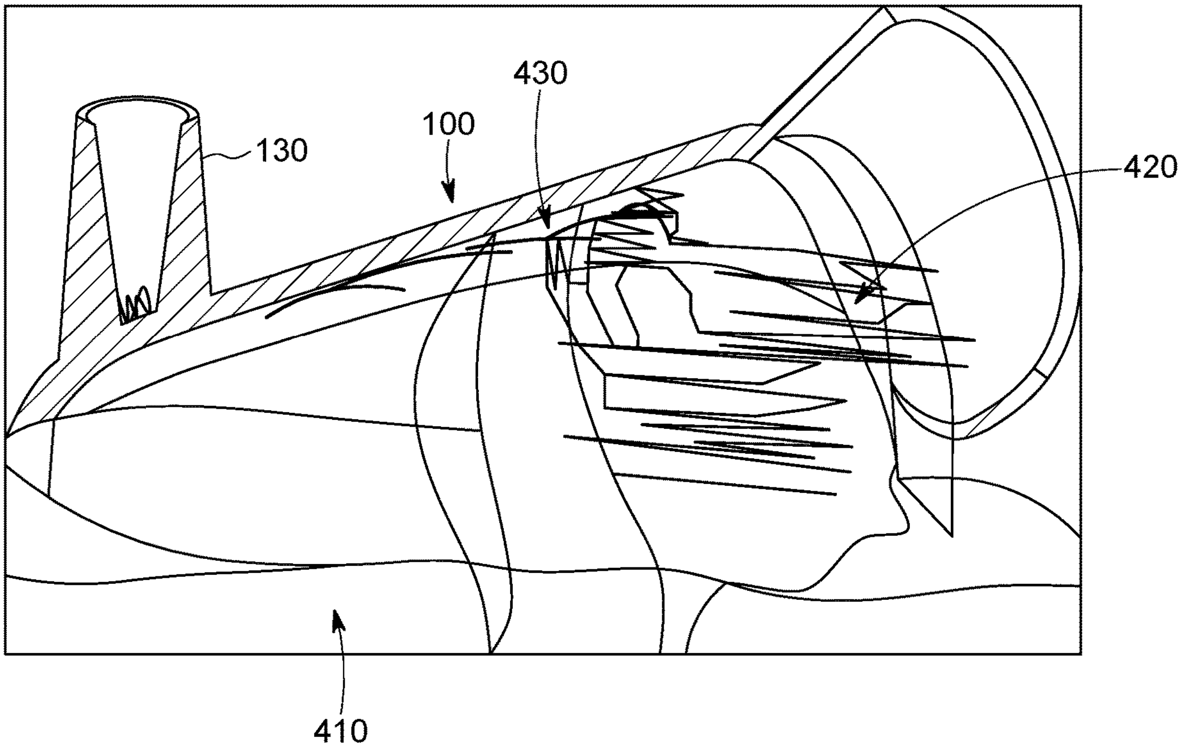
FIG. 4 is diagram showing a side view of a simulation of the motion of particles in a sneeze by the patient through the nasal guard of FIG. 1.
Figure 4A:
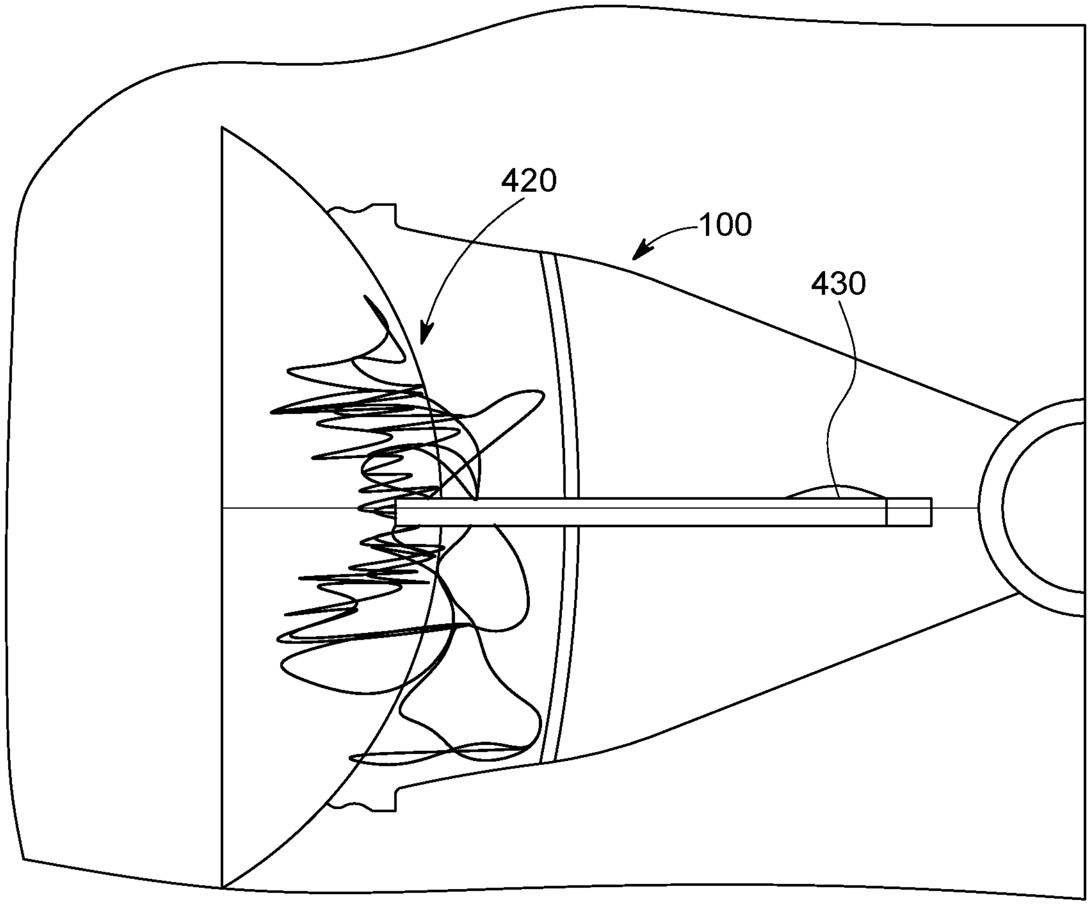
FIG. 4A is diagram showing a top view of the simulation of the motion of particles in a sneeze by the patient through the nasal guard of FIG. 4.

With reference to FIGS. 4 and 4A, a computer simulation of the performance of the nasal guard 100, according to an embodiment herein, with 5 μm particles generated at nostril set to escape the inlet at 4.5 m/s sneezing velocity—but being captured by the vacuum flow (trace 430). The particle motion is depicted as a trace 420. FIG. 4 shows an oblique view with face 410 at the bottom. FIG. 4A shows a top-down view of the guard 100 with associated particle and vacuum traces 420 and 430, respectively.

Figure 5:
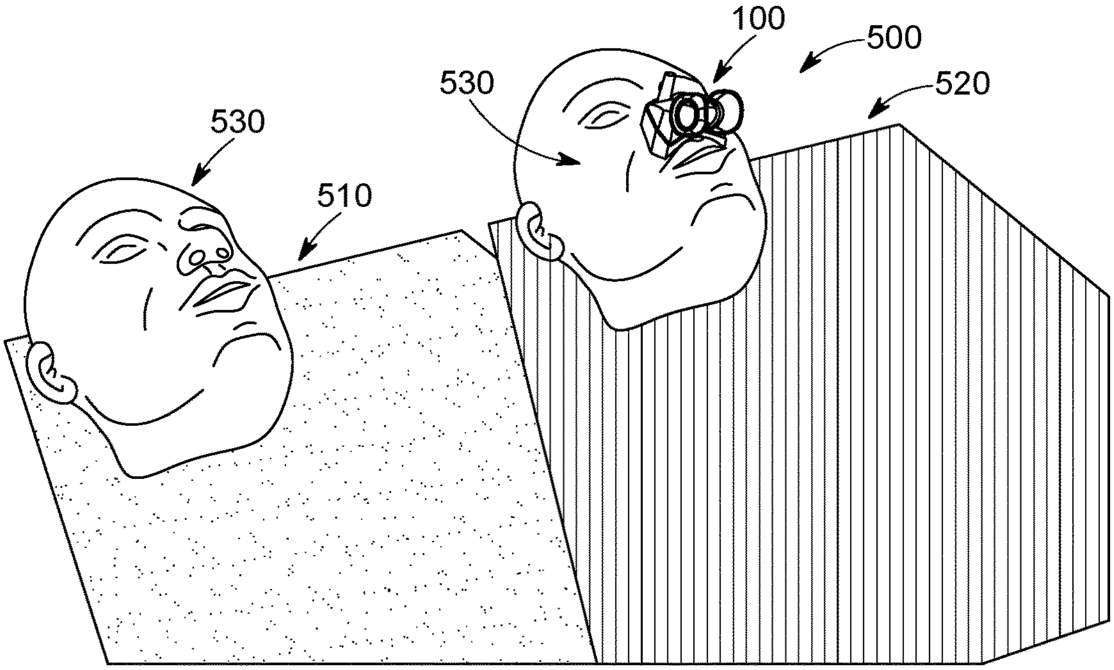
FIG. 5 is a diagram of a computer simulation used to prove the effectiveness of the nasal guard of FIG. 1 and further embodiments thereof.

FIG. 5 shows a diagram 500 of an experimental setup that can be used to test the effectiveness of the present embodiment of the nasal guard 100, and assist in improving and refining the nasal guard concept. The left side 510 of the diagram shows fluorescent splatter in control and the right side 520 shows the setup with the nasal guard 100 in place on the patient's face 530.

Figure 6:
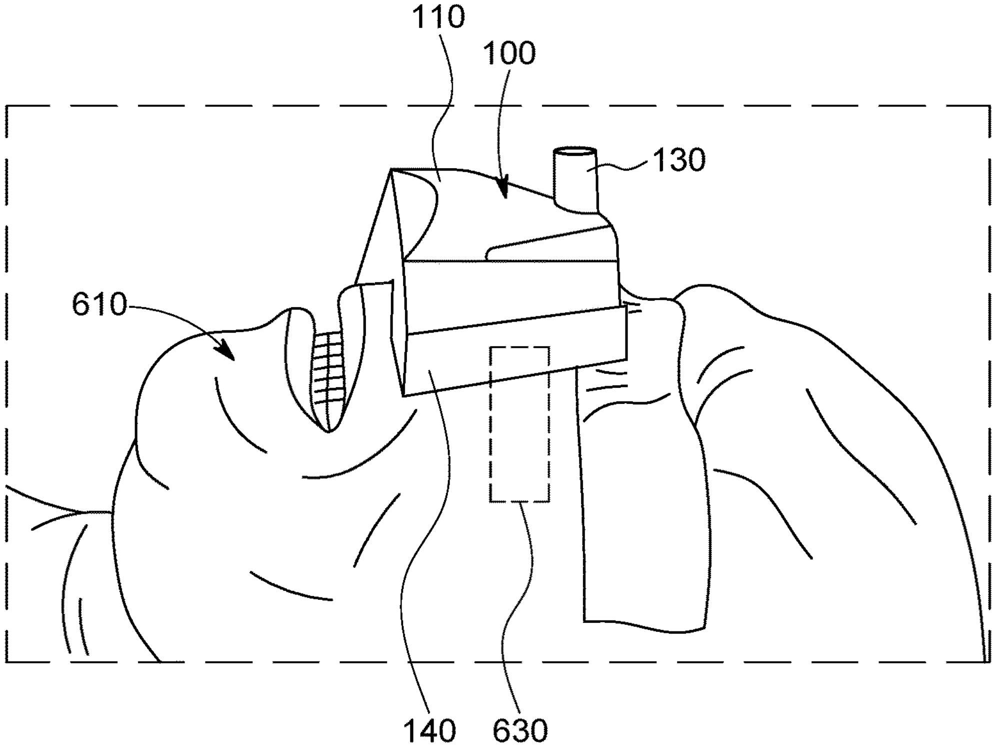
FIG. 6 is a side view showing placement of the nasal guard of FIG. 1 on an exemplary patient's face.

FIG. 6 further depicts the side profile of a patient's face 610 with the nasal guard 100 fitted thereon. Note that the guard can be adhered by friction between the face 610 and the pliable/resilient (e.g. silicone) base 140, combined with the bias of the suction flow generated by the vacuum. Alternatively, or additionally, the nasal guard 100 can be secured using a fixation mechanism such as an adjustable strap that is passed around the head and/or medical-grade tape 630 (shown in phantom).

More particularly, to test and validate the performance of the illustrative embodiment and improvements thereof, a cadaver study can be beneficial, and assist in determining the actual reduction in aerosolized emission during a simulated surgery compared to standard conditions. A burst of pressured air can simulate the aerosolization that occurs surgical drilling in the nose. Fluorescein dye placed within the nares can act as probe to analyze the splatter in surrounding field under ultraviolet fluorescence. The test can involve measurement of the amount of dye escaped from the nasal shield and the distribution and range of the splatter. Using such results, an iterative design process can be employed to improve performance of the illustrative nasal guard (e.g. cavity shape, seal geometry, etc.) under simulated conditions.

In development, Solidworks® (for example) solid-modeling software or a similar CAD program can be used to design the nasal guard geometry and to simulate its function in-silico. By way of example, a prototype of the illustrative nasal guard can be 3-D printed in durable resin using a Form 3 printer by Formlabs. The underlying silicone gasket can be cast from Ecoflex™ 00-30 biocompatible silicone by Smooth-on to create a seal around patient's face. The present design can be further modified through iterative testing with feedback from surgeons and practitioners in the field.

Figure 7:
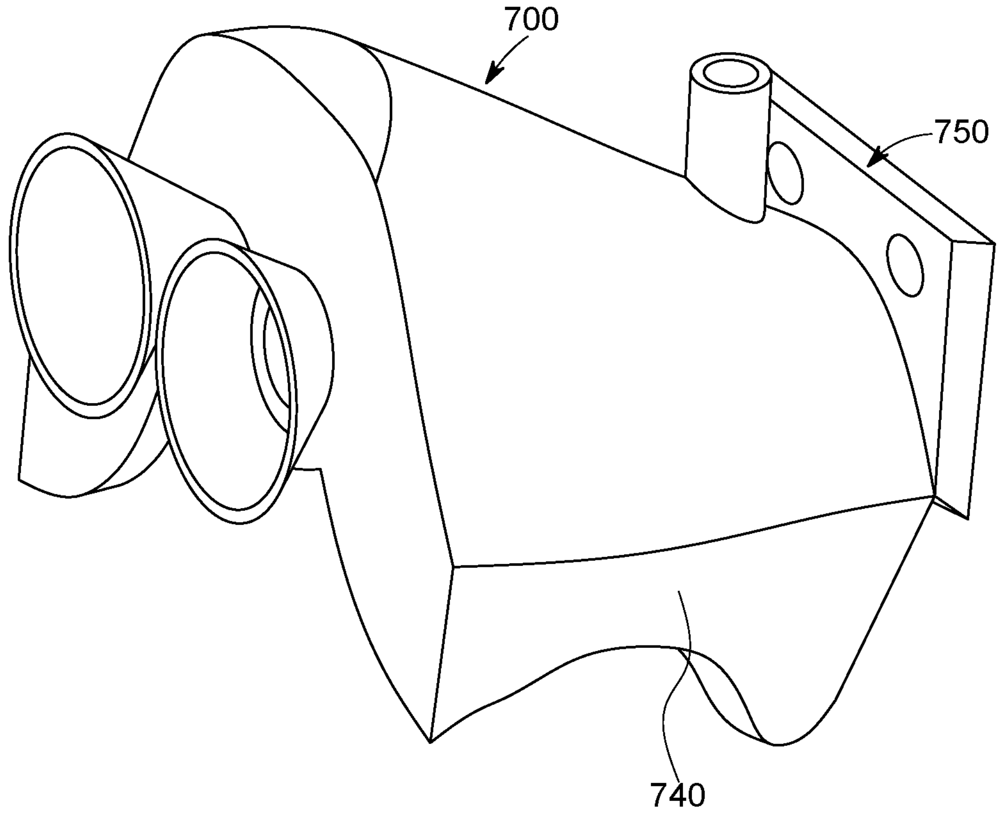
FIG. 7 is a perspective view of a nasal guard according to an alternate embodiment.
Figure 8:
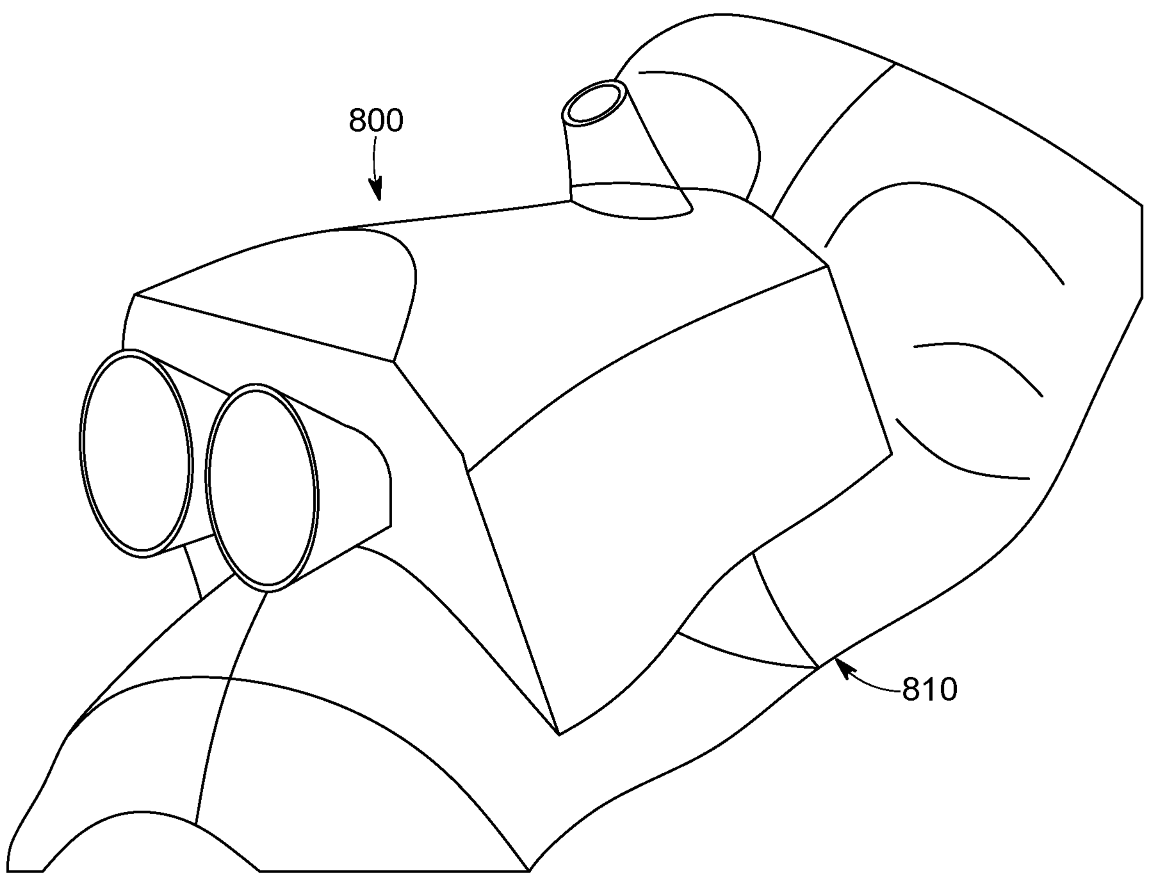
FIG. 8 is a perspective view of the nasal guard generally as shown in FIG. 7 placed on an exemplary patient's face.

FIG. 7 shows an alternate embodiments of the nasal guard 700 in which the base is molded with a curve to conform more closely to the face. An optional plate 750 can be provided adjacent to the vacuum inlet 760 for securing various components, such as a vacuum hose or hold down straps. A similar guard 800 is shown secured to a face 810 in FIG. 8. These embodiments can perform the various functions of guiding instruments and removing fluid/particulate contaminants in a manner described above. In another alternate embodiment (not shown) it is contemplated that only one (right or left) nostril is exposed for insertion of an instrument through an opening, and the other opening is permanently or removably (e.g. using a removable plug, cap, etc.) sealed so that the vacuum flow can be reduced and/or concentrated relative one opening, also, while the top section of the nasal guards herein has a shape that somewhat matches the contours of the nose (i.e. an irregular dome or pyramidal shape), the shape of the top section can be highly variable in alternate embodiments—for example a regular or irregular box, frustum, etc. It is mainly desirable that one or both nostrils be accessible via a confronting opening and the vacuum flow be routed away from that opening using an appropriate internal cavity geometry. Such geometry generally allows for airflow via vacuum suction across the top of the nose (and optionally around the sides of the nose) to the outlet port.

It should be clear that the above-described nasal guard provides an effective and easy to use device for reducing the risk of contamination from aerosolized particulates while performing nasal surgery.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated, new embodiments. Furthermore, while the foregoing describes a number of separate embodiments of the apparatus and method of the present invention, what has been described herein is merely illustrative of the application of the principles of the present invention. For example, as used herein various directional and dispositional terms such as "vertical", "horizontal", "up", "down", "bottom", "top", "side", "front", "rear", "left", "right", and the like, are used only as relative conventions and not as absolute directions/dispositions with respect to a fixed coordinate space, such as the acting direction of gravity. Additionally, where the term "substantially" or "approximately" is employed with respect to a given measurement, value or characteristic, it refers to a quantity that is within a normal operating range to achieve desired results, but that includes some variability due to inherent inaccuracy and error within the allowed tolerances of the system (e.g. 1-5 percent). Accordingly, this description is meant to be taken only by way of example, and not to otherwise limit the scope of this invention.

What is claimed is:

1. A nasal guard for placement on a patient's face during surgical procedures comprising:

a rigid or semi-rigid top section with channels for access to the nostrils by surgical instruments;

a frustoconical instrument guiding shroud for each of the channels respectively flared outwardly from the top section;

a vacuum port in communication by vacuum flow with the channels;

a cavity formed in the top section connecting the vacuum port with the channels, the cavity establishing a region of the top section for evacuation, via the vacuum flow, of materials proximal to the channels through the vacuum port; and a soft pliable base located between the rigid or semi-rigid section and the patient's face.

2. The nasal guard as set forth in claim 1 wherein the top section is constructed from a polymer material.

3. The nasal guard as set forth in claim 1 wherein the base is constructed from a silicone-based compound.

4. The nasal guard as set forth in claim 3 wherein the base defines a contoured edge constructed and arranged to sealingly conform to the patient's face around a nose thereof.

5. The nasal guard as set forth in claim 1 wherein the surgical instruments include nasal endoscopes.

6. The nasal guard as set forth in claim 1 wherein the vacuum port is located on a top of the top section adjacent to a side thereof opposite the channels and the vacuum port is constructed and arranged for removable attachment of a vacuum line.

7. The nasal guard as set forth in claim 1 wherein the frustoconical shroud is unitarily molded with the channels when forming the top section.

8. The nasal guard as set forth in claim 1 wherein the frustoconical shroud is integrally applied to the top section and aligned with the channels.

9. The nasal guard as set forth in claim 1 wherein the top section comprises 3D printed materials with shape/sizing thereof derived from contours of the patient's face.

10. The nasal guard as set forth in claim 1 wherein the evacuation of materials proximal to the channels enabled by the cavity through the vacuum port evacuates 5 μm sized particles generated at least 4.5 m/s sneezing velocity from one or more of the nostrils via the vacuum flow.

11. The nasal guard as set forth in claim 1 wherein the nasal guard adheres by friction between the patient's face and the base combined with a bias of the suction flow enabled by the cavity.

12. The nasal guard as set forth claim 1 further comprising a surgical component retaining plate proximal to the vacuum port for securing one or more surgical components.

13. A nasal guard for placement on a patient's face during nasal surgical procedures, the nasal guard comprising:

a plurality of channels connecting a top surface of a top section through a cavity formed in the top section, the plurality of channels connecting through a bottom surface of the top section of the nasal guard;

an instrument guiding shroud for each of the channels respectively flared outwardly from the top section; and a vacuum port formed in the top surface, wherein the cavity formed between the top surface and the bottom surface of the top section establishes a region of the top section that connects the vacuum port with the plurality of channels, thereby facilitating evacuation, via vacuum flow, of materials proximal to the channels through the vacuum port.

14. The nasal guard as set forth in claim 13, wherein the nasal guard is constructed from a polymer material.

15. The nasal guard as set forth in claim 13 wherein the bottom surface defines a contoured edge constructed and arranged to sealingly conform to a patient's face around a nose thereof.

16. The nasal guard as set forth in claim 13 wherein the shroud is frustoconical and the shroud is unitarily molded with the channels when forming the top section.

17. The nasal guard as set forth in claim 13 wherein the shroud is frustoconical and the shroud is integrally applied to the top section and aligned with the channels.

18. The nasal guard as set forth in claim 13 wherein the top section comprises 3D printed materials with shape/sizing thereof derived from contours of the patient's face.

19. The nasal guard as set forth in claim 13 wherein the evacuation of materials proximal to the channels enabled by the cavity through the vacuum port evacuates particles generated at a sneezing velocity from one or more of the nostrils via the vacuum flow.

20. The nasal guard as set forth in claim 13 wherein the nasal guard adheres by friction between the patient's face and the base combined with a bias of the suction flow enabled by the cavity.

* * * * *